United States Patent
Nirschl

(10) Patent No.: US 9,140,668 B2
(45) Date of Patent: Sep. 22, 2015

(54) DEVICE AND METHOD FOR DETECTING AT LEAST ONE SUBSTANCE

(75) Inventor: Martin Nirschl, Traunstein (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 632 days.

(21) Appl. No.: 13/499,074

(22) PCT Filed: Aug. 10, 2010

(86) PCT No.: PCT/EP2010/061627
§ 371 (c)(1),
(2), (4) Date: Mar. 29, 2012

(87) PCT Pub. No.: WO2011/038972
PCT Pub. Date: Apr. 7, 2011

(65) Prior Publication Data
US 2012/0184051 A1   Jul. 19, 2012

(30) Foreign Application Priority Data

Sep. 30, 2009   (DE) .......................... 10 2009 047 807

(51) Int. Cl.
*G01N 29/02* (2006.01)
*G01N 29/036* (2006.01)
*H03H 9/17* (2006.01)

(52) U.S. Cl.
CPC ............ *G01N 29/022* (2013.01); *G01N 29/036* (2013.01); *G01N 2291/0256* (2013.01); *G01N 2291/0426* (2013.01); *G01N 2291/0427* (2013.01); *H03H 9/175* (2013.01)

(58) Field of Classification Search
CPC ........................... G01N 29/022; G01N 29/036
See application file for complete search history.

(56) References Cited

U.S. PATENT DOCUMENTS

| | | | |
|---|---|---|---|
| 2004/0183400 A1* | 9/2004 | Aigner et al. | 310/326 |
| 2005/0104690 A1* | 5/2005 | Larson et al. | 333/191 |
| 2006/0125489 A1 | 6/2006 | Feucht et al. | 324/633 |
| 2006/0232361 A1 | 10/2006 | Bradley | 333/133 |
| 2007/0285191 A1* | 12/2007 | Jacobsen | 333/187 |

(Continued)

FOREIGN PATENT DOCUMENTS

| | | | |
|---|---|---|---|
| DE | 10308975 B4 | 2/2004 | G01N 29/02 |
| DE | 102004035812 A1 | 3/2006 | H03H 9/17 |
| WO | 2007/071233 A1 | 6/2007 | H03H 9/17 |

OTHER PUBLICATIONS

Dickherber, A., et al., "Optimization and Characterization of a ZnO Biosensor Array", ScienceDirect, Sensors and Actuators A Physical, vol. 144, pp. 7-12, Jan. 19, 2008.

(Continued)

*Primary Examiner* — Melanie Y Brown
(74) *Attorney, Agent, or Firm* — Slayden Grubert Beard PLLC

(57) ABSTRACT

A device for detecting at least one substance may include a resonator which, on its surface facing away from the carrier, is provided with a chemically sensitive layer for selectively binding a substance that is to be detected. An acoustic mirror is arranged between the carrier and the resonator. The acoustic mirror constitutes a band elimination filter having two closely adjacent notch frequencies, as a result of which the device is capable of oscillating in two resonant frequencies. The mass binding of the substance and the temperature can be determined computationally from the measured resonant frequencies.

16 Claims, 7 Drawing Sheets

(56) References Cited

U.S. PATENT DOCUMENTS

2008/0258845 A1   10/2008  Schmidhammer ............ 333/195
2009/0002098 A1    1/2009  Mayer et al. .................. 333/189
2010/0127600 A1*  5/2010  Loschonsky et al. .... 310/323.21

OTHER PUBLICATIONS

German Office Action, German Patent Application No. 10 2009 047 807.8-52, 4 pages, Mar. 31, 2010.
International PCT Search Report and Written Opinion, PCT/EP2010/061627, 15 pages, Dec. 1, 2010.

* cited by examiner

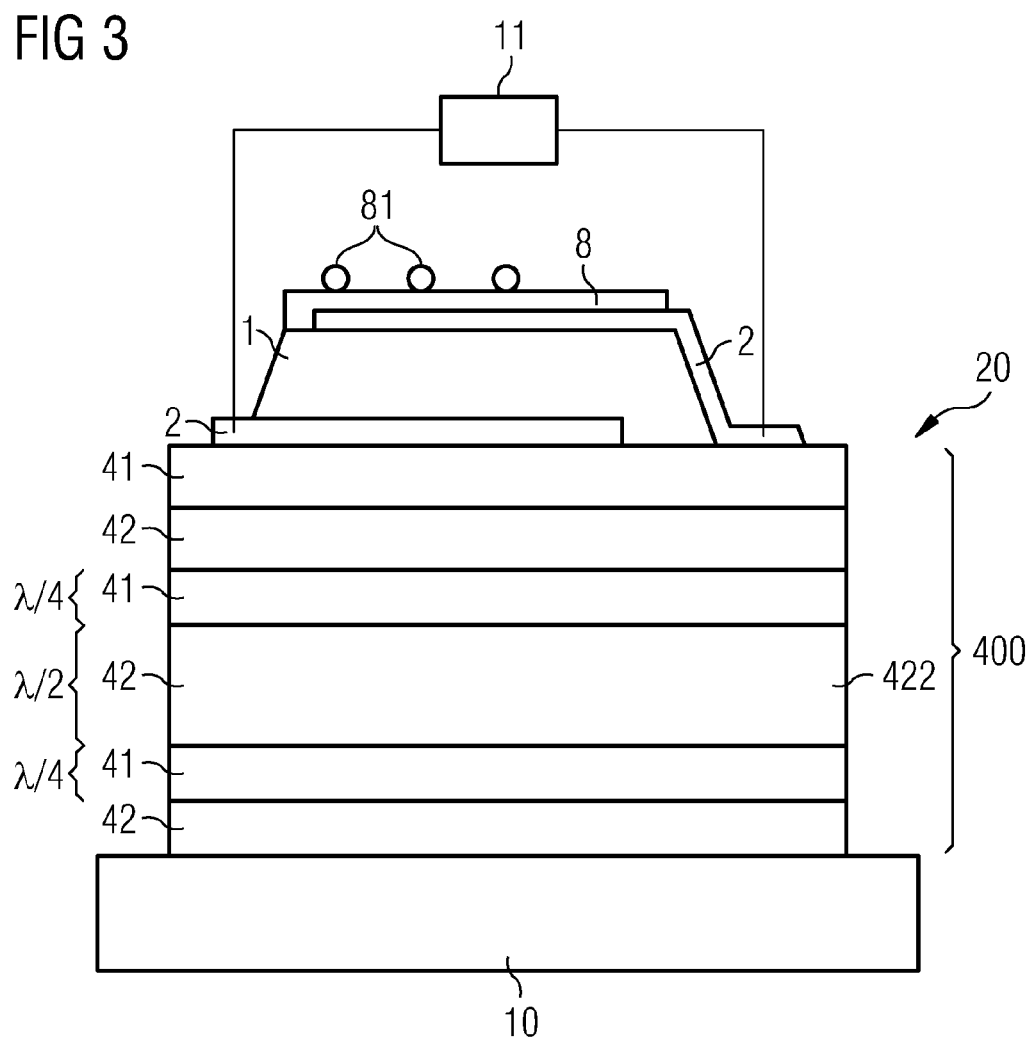

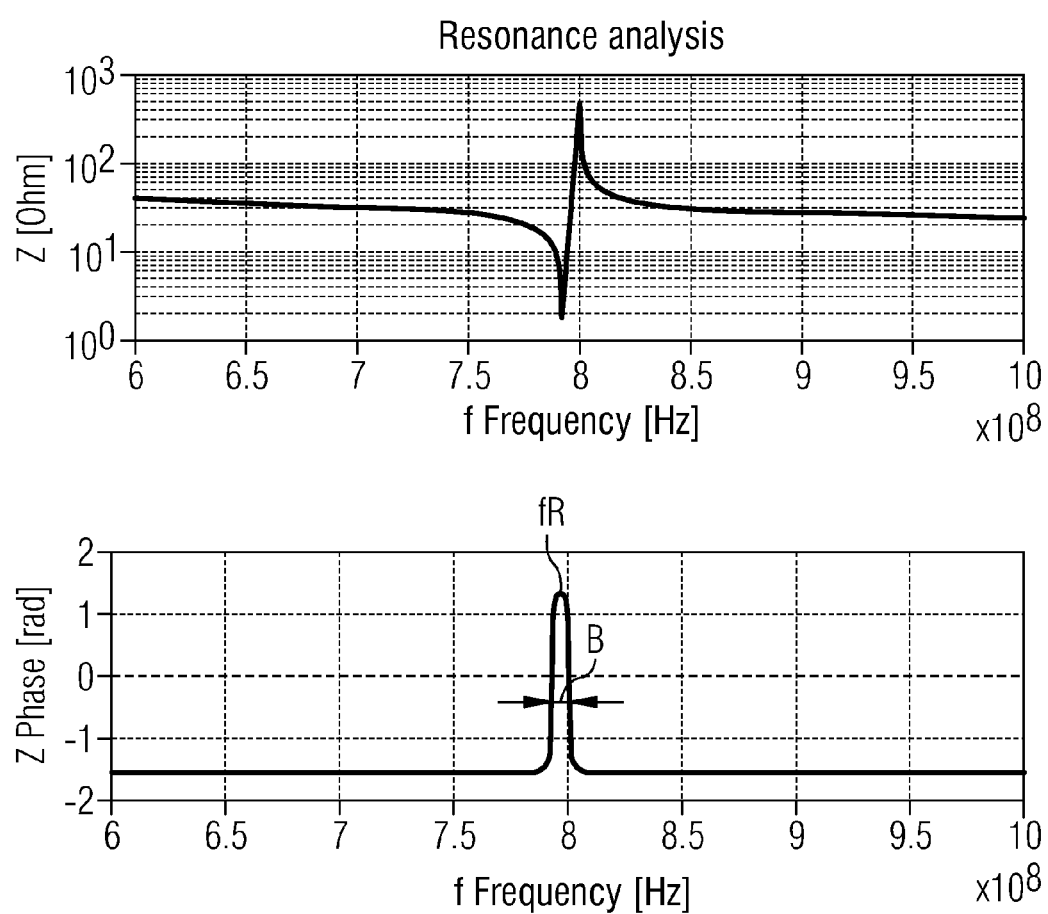

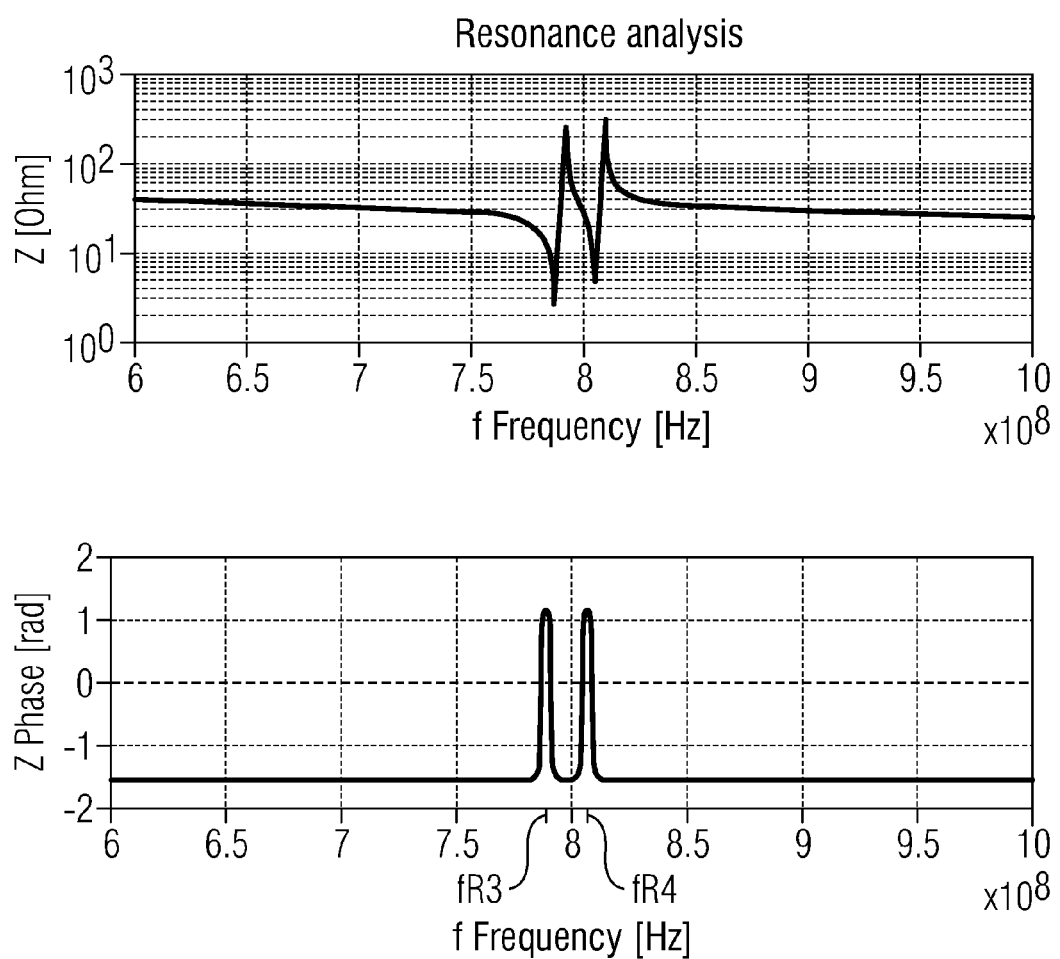

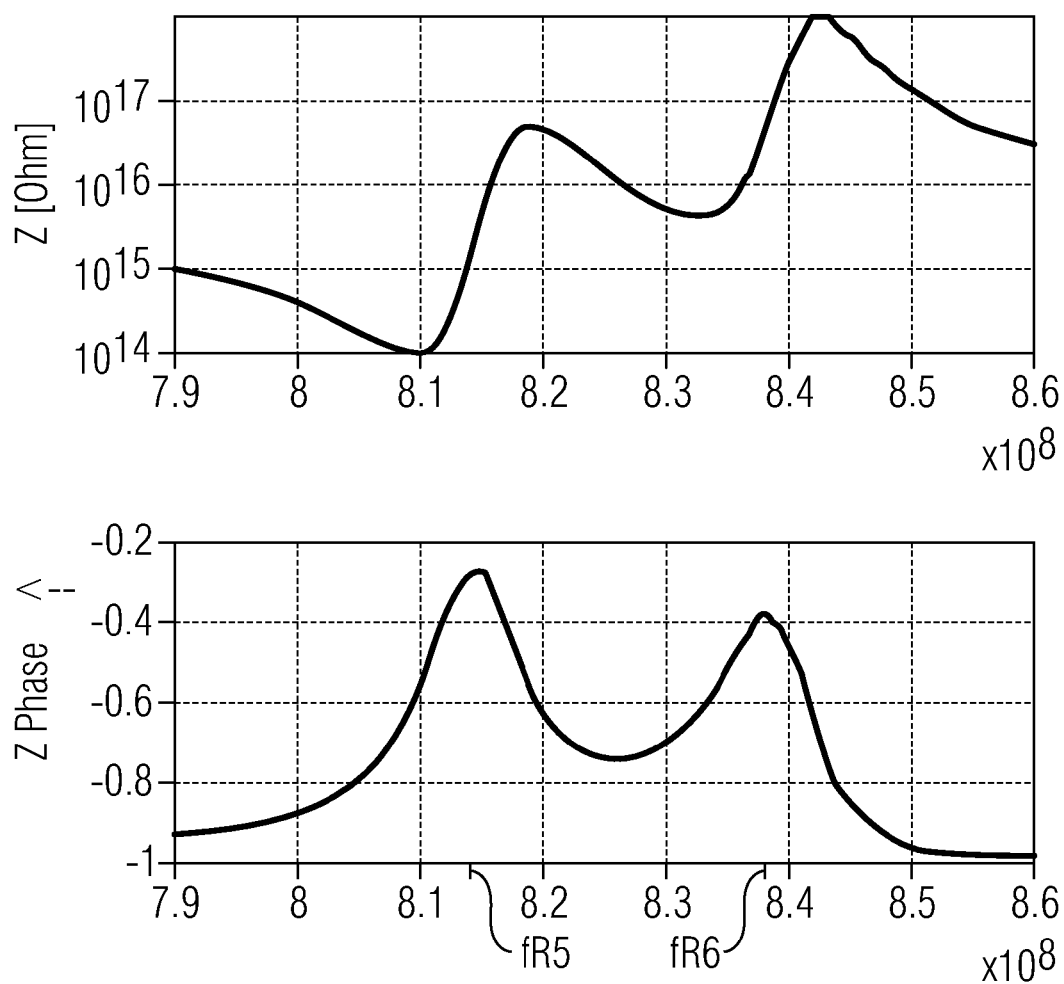

DEVICE AND METHOD FOR DETECTING AT LEAST ONE SUBSTANCE

CROSS-REFERENCE TO RELATED APPLICATIONS

This application is a U.S. National Stage Application of International Application No. PCT/EP2010/061627 filed Aug. 10, 2010, which designates the United States of America, and claims priority to DE Patent Application No. 10 2009 047 807.8 filed Sep. 30, 2009. The contents of which are hereby incorporated by reference in their entirety.

TECHNICAL FIELD

This disclosure relates to a device and a method for detecting at least one substance.

BACKGROUND

In the chemical or pharmaceutical industry it is often important to conduct analyses of substances in a fluid with a small sample quantity and a high throughput.

DE 10308975B4 discloses a piezoelectric resonator whose resonant frequency changes when a fluid containing substances is applied to the surface of the resonator, said substances being adsorbed by the resonator surface. The technology employed to build the resonator is also referred to as "film bulk acoustic wave resonator" (FBAR). The substance present in the fluid is absorbed by the chemically sensitive surface of the resonator. The concentration of the substance in the fluid can be determined by measuring the change in resonant frequency. In most cases it is merely desired to ascertain one parameter, such as the mass binding of the substance, as a result of which the concentration of the substance in the fluid can also be deduced.

The other parameters which can influence the resonant frequency are interference effects. For example, the resonator frequency changes for example as a function of the temperature, mechanical stress or vibration. In certain conventional systems these undesirable effects must be kept constant during the measurement. This may be achieved for instance by means of a heating system which keeps the sensor/acoustic resonator at a constant temperature. In addition the measurement setup may be mounted on a stable base in order to avoid forms of interference caused by vibrations.

One possibility of reading out temperature and mass binding simultaneously or of measuring the same with the aid of the acoustic resonator is to measure the temperature separately from the resonator, with a platinum resistor for instance. This method is often inaccurate due to the measuring imprecision and inertia of the sensor.

SUMMARY

In an embodiment, a device for detecting at least one substance comprises a carrier, a resonator which is applied to the carrier and which on its surface facing away from the carrier is provided with a layer for selectively or non-selectively binding a substance requiring to be detected, wherein an acoustic mirror for decoupling the acoustic waves of the resonator from the carrier is arranged between the carrier and the resonator, wherein the acoustic mirror constitutes a band elimination filter having two adjacent notch frequencies at which the waves of the resonator are at least partially reflected, wherein in particular more than two notch frequencies are present.

In a further embodiment, at almost one hundred percent decoupling from the carrier the resonant frequency of the resonator lies between the two notch frequencies of the mirror. In a further embodiment, the resonator is acoustically coupled to the carrier via the mirror such that the resonant frequency of the device is detuned from the resonant frequency of the resonator in the direction of the two notch frequencies of the mirror to a first and a second resonant frequency of the device. In a further embodiment, the resonator has a thickness which is equivalent to half the resonance wavelength of the resonator at almost one hundred percent decoupling from the carrier. In a further embodiment, starting from the resonator the acoustic mirror has a layer having higher acoustic impedance and a layer having lower acoustic resonance alternating with one another in multiple sequence, wherein the thicknesses of the layers are in each case approximately equivalent to a quarter of the wavelength of the resonant frequency of the resonator, wherein at least one of the layers having the low acoustic impedance or the higher acoustic impedance has a thickness between a quarter and half of the inverse of the resonant frequency of the resonator.

In a further embodiment, starting from the resonator the layer having the greater thickness represents the second, fourth or sixth layer. In a further embodiment, the resonator can be excited by means of electrical energy, contains a piezoelectric element as the active element and may be embodied as a film bulk acoustic wave resonator (FBAR), the resonator being provided with electrical terminals to allow the electrical energy to be supplied. In a further embodiment, an evaluation unit is present for electrically driving the resonator and for measuring the current frequency, in particular the resonant frequencies, at a given time. In a further embodiment, the difference between the two resonant frequencies of the device lies between a seventh and a twentieth of the arithmetic mean of the two resonant frequencies. In a further embodiment, the mass sensitivity at the first resonant frequency is different from the mass sensitivity of the second resonant frequency, and/or the temperature sensitivity at the first resonant frequency is different from the temperature sensitivity of the second resonant frequency, such that the mass binding ($\Delta m$) and the change in temperature ($\Delta T$) can be determined by measuring the current resonant frequencies or their shifts ($\Delta fR1$, $\Delta fR2$) with respect to predefined reference resonant frequencies at a predefined reference temperature and a predefined reference mass, wherein the measurements of the resonant frequencies are taken sequentially with a negligible time offset in each case, negligible without a change in temperature and/or change in mass occurring in this time period.

In a further embodiment, the current mass binding ($\Delta m$) of the substance to be detected to the layer and/or the current change in temperature ($\Delta T$) can be determined with the aid of the following formulae:

$$\Delta m = \frac{\Delta fR1 * kT2 - \Delta fR2 * kT1}{km2 * kT1 - km1 * kT2} \qquad \text{(Equation 1)}$$

$$\Delta T = \frac{\Delta fR1 * km2 - \Delta fR2 * km1}{km2 * kT1 - km1 * kT2|} \qquad \text{(Equation 2)}$$

where
$\Delta fR1$: change in the first resonant frequency of the device with respect to a preliminary value or reference value,
$\Delta fR2$: change in the second resonant frequency of the device with respect to a preliminary value ( ) or reference value,
$km1$: mass sensitivity at the first resonant frequency of the device km2: mass sensitivity at the second resonant frequency of the device
kT1: the temperature sensitivity at the first resonant frequency of the device
kT2: the temperature sensitivity at the second resonant frequency of the device.

In a further embodiment, the mass sensitivity km is defined as follows:

$$km = \Delta f/\Delta m = cm * fR/m \cong fR^2 \qquad \text{(Equation 3)}$$

where km is the mass sensitivity of the device, fR the resonant frequency of the device without adsorbed substance, cm a material-specific constant, and m the mass of the resonator per unit area, the mass sensitivity km being proportional to the square of the resonant frequency fR of the device; the temperature sensitivity kT is defined as follows:

$$kT = \Delta f/\Delta T = cT * fR/T \qquad \text{(Equation 4)}$$

where kT is the temperature sensitivity of the device, fR the resonant frequency of the device at a predefined reference temperature (T_ref), cT a material-specific constant, and T the temperature of the resonator or of the device.

In another embodiment, a method is provided for detecting at least one substance with the aid of a device as discussed above, wherein the resonator is driven by means of a multi-frequency spectrum for the purpose of measuring two or more current resonant frequencies in the region of the same.

In a further embodiment, in order to measure the mass binding/mass of the substance the two closely adjacent resonant frequencies are measured close to each other in time, and the mass binding and the temperature are computationally extracted from the two measured resonant frequencies, wherein in particular the concentration of a substance from a fluid can be measured from the mass binding. In a further embodiment, the temperature of the resonator/of the sensor/of the device is changed, the two resonant frequencies of the device are measured continuously, from which the current temperature T or the change in temperature ΔT and the current mass binding (Δm) are determined, as a result of which a multiplicity of biological and chemical processes can be determined, for example the determination of the melting temperature of DNA, the investigation of the thermal resistance of substances, in particular proteins (heat shock proteins).

In a further embodiment, the mass binding (Δm) is determined with computational extraction of the fluctuations (ΔT) in the temperature, even if the ambient temperature varies or the sensor/device itself heats up. In a further embodiment, in respect of the mass binding (Δm), instead of or in addition to determining the change in temperature (ΔT), a further parameter change, e.g., mechanical deformation or vibrations, is determined computationally.

BRIEF DESCRIPTION OF THE DRAWINGS

Example embodiments will be explained in more detail below with reference to figures, in which:

FIG. 3 shows a further variant of the example device of FIG. 1 having a slightly detuned acoustic mirror, FIG. 4a is a diagram representing the impedance-frequency dependence of the example device of FIG. 1, FIG. 4c is a diagram representing the impedance-frequency dependence of the example device of FIG. 3, and FIG. 4d is a diagram containing measurement results of the impedance-frequency dependence of a further device from FIG. 2.

DETAILED DESCRIPTION

Figure 1:
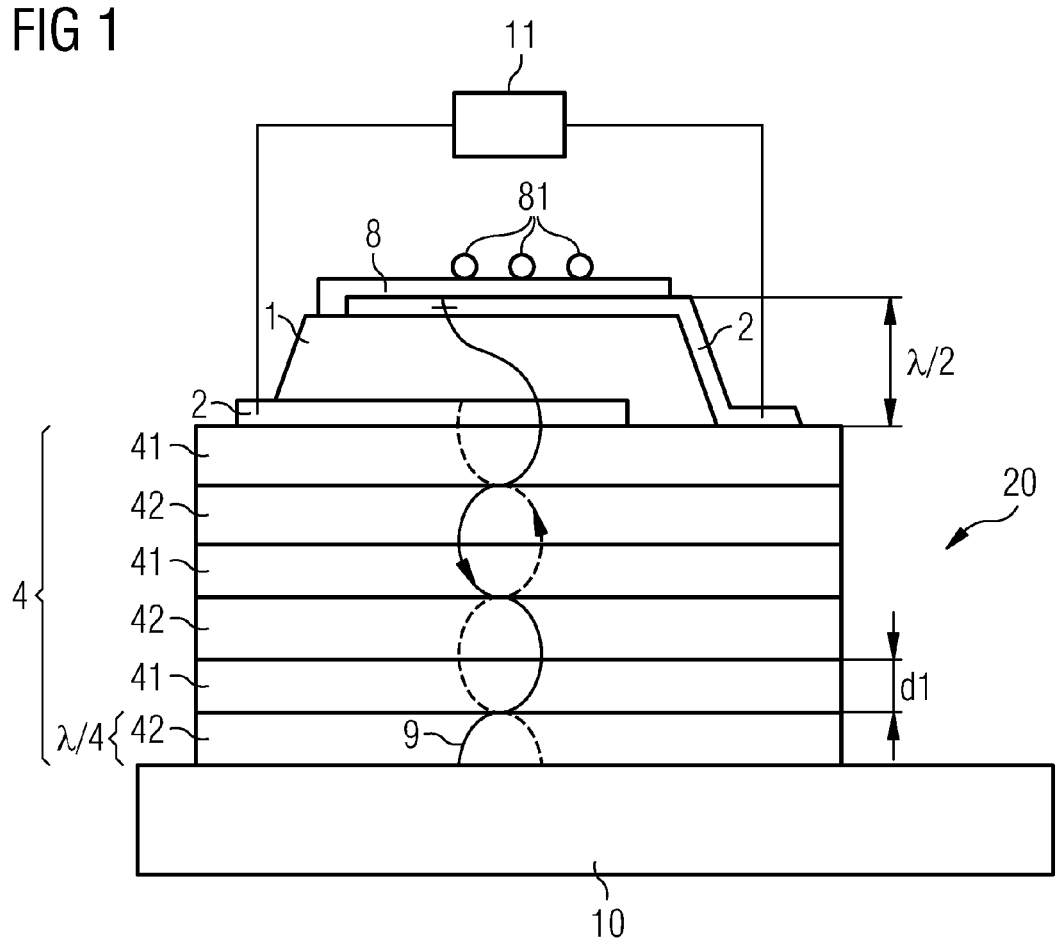
FIG. 1 shows a schematic cross-section of an example device for detecting a substance, comprising a resonator applied to a carrier and an acoustic mirror arranged therebetween.

Some embodiment provide a device and a method for detecting a substance in which a plurality of parameters of the device can be measured without the aid of auxiliary means.

Sorption is to be understood as the formation of a chemical or physical bond binding the substance to the surface section. The term sorption encompasses both absorption and adsorption. In absorption the substance is assimilated for example by a coating of the resonator that forms the surface section, without forming a phase boundary. The substance is incorporated into the coating. In adsorption, by contrast, the process results in the formation of a phase boundary.

Conceivable in particular in this context is adsorption in the form of physisorption. The substance becomes attached to the surface section of the resonator as a result of van der Waals or dipole-dipole interactions. Alternatively thereto, adsorption in the form of chemisorption can also take place.

In chemisorption the substance accumulates on the surface section while forming a chemical bond. The chemical bond is for example a covalent bond or a hydrogen bridge bond.

Preferably the sorption takes place reversibly. This means that the substance can also be desorbed (removed) from the surface section again. For example, the substance is removed again by increasing the temperature of the surface section or by the action of a reactive substance. The reactive substance is for example an acid or an alkaline solution with the aid of which the bonds formed during the chemisorption are released. This enables the device to be used more than once. It is, however, also possible for the sorption to be irreversible. The device is used once only as a single-use sensor.

The below-mentioned fluid is formed for example from an aqueous solution or as a hydrocarbon-based solvent. However, it can also be a gas having a gas component that is to be detected. Every conceivable chemical or biological compound is a suitable candidate substance. Thus, the device can be used as a gas sensor for detecting a gas. The gas is a substance which has a specific vapor pressure. Substances of said kind are for example organic solvents. It is also conceivable that such a substance is an explosive or a component, a preliminary product or a decomposition product of an explosive. The device can be used as an explosives detector. It is also conceivable that the device is embodied as a biosensor for detecting an arbitrary biomolecule. The biomolecule is for example a DNA (Deoxyribonucleic Acid) sequence or a macromolecular protein.

The surface section may be embodied in such a way that a specific substance or substance class is selectively sorbed in accordance with the key-lock principle and accordingly identified. In this way it is possible with the aid of the device to selectively detect a specific substance from a mixture composed of a multiplicity of substances. In this case the detection comprises both a qualitative and a quantitative determination of the substance. The absence or presence of the substance in the fluid can be demonstrated. The concentration of the substance in the fluid can also be determined. A change in the concentration of the substance over time can also be determined by differential detection of the substance.

Accordingly, the device is also suitable for example for reaction monitoring of a chemical reaction in which the substance is involved.

However, the surface section can also be provided with a material for selective or non-selective binding of a substance that is to be detected, which material is not or not only chemically sensitive, but specifically selective or non-selective and/or sorption-capable for a substance that is to be detected or a reaction or hybrid product. Alternatively the material can be capable of assimilating accumulations or deposits of the aforementioned substances.

In particular the chemically sensitive coating has molecules for detecting the substance. In order to identify a specific DNA sequence, such molecules are corresponding oligonucleotides (oligos) consisting of a plurality of nucleotides.

In this case the molecules for detecting the substance can be directly bonded to a transducer surface. For example, the transducer surface is a gold electrode of the resonator. Molecules possessing a thiol group are directly bound to the transducer surface by development of a gold-sulfur bond.

In the case of an acoustic mirror, use is made of the technique of Bragg mirrors that is known from optics, in which light waves are reflected by stacked thin layers whose thickness is approximately equivalent to a quarter of the light wavelength. For this purpose the actual resonator is supported by a sequence of further thin layers stacked one on top of another and having alternately low and high acoustic impedance. These layers act as acoustic reflectors, also referred to as acoustic mirrors, and acoustically decouple the resonator from the carrier substrate. The acoustic impedance Z of a layer is defined here as $Z=\sigma*v$, where $\sigma$ denotes the density of the layer and v the propagation speed or sound velocity of the acoustic wave. The mirror thus constitutes a band elimination filter whose notch frequency is embodied such that it coincides with the resonant frequency of the resonator. Silicon slices (wafers) having a high ohmic resistance or high impedance are preferably used as the carrier substrate of the resonator and the acoustic mirror.

In some embodiments, the device for detecting at least one substance has a carrier onto which is applied a resonator which is provided with a chemically sensitive layer on its surface facing away from the carrier for the purpose of selectively binding a substance that is to be detected. An acoustic mirror is arranged between the carrier and the resonator for the purpose of decoupling the acoustic waves of the resonator from the carrier. The acoustic mirror is embodied as a band elimination filter having two adjacent notch frequencies at which the waves of the resonator are at least partially reflected. The device is in resonance at two measurable frequencies, as a result of which both the mass binding and changes in temperature can be determined computationally. Alternatively, more than two notch frequencies with resonant frequencies resulting therefrom are also possible, as a result of which more than two parameters can be determined.

At almost one hundred percent decoupling from the carrier, the resonant frequency of the resonator preferably lies between the two notch frequencies of the mirror, thereby achieving a high quality of the resonant oscillating circuits.

The resonator may be acoustically coupled to the carrier via the mirror such that the resonant frequency of the device is detuned from the resonant frequency of the resonator in the direction of the two notch frequencies of the mirror to a first and a second resonant frequency of the device.

The resonator has a thickness equivalent to half the resonance wavelength of the resonator at almost one hundred percent decoupling from the carrier, thereby enabling resonant frequencies of the device to be easily determined with a high degree of quality.

Starting from the resonator, the acoustic mirror has a layer having higher acoustic impedance and a layer having lower acoustic resonance alternating with one another in multiple sequence, wherein the thicknesses of the layers are in each case approximately equivalent to a quarter of the wavelength of the resonant frequency of the resonator,
wherein at least one of the layers having the low acoustic impedance or the higher acoustic impedance has a thickness between a quarter and half of the wavelength in the resonator. This enables tried-and-tested fabrication processes to be used.

Starting from the resonator, the layer with the greater thickness constitutes the second, fourth or sixth layer. This likewise allows tried-and-tested fabrication processes to be used.

The resonator can be excited by means of electrical energy and contains a piezoelectric element as active element; it may be embodied as a film bulk acoustic wave resonator (FBAR), the resonator being provided with electrical terminals to allow the electrical energy to be supplied.

An evaluation unit is present for electrically driving the resonator and for measuring the current frequency, in particular the resonant frequencies, at a given time. The measurement and computational results are effectively available online as a result.

The difference between the two resonant frequencies of the device lies between a seventh and a twentieth of the arithmetic mean of the two resonant frequencies, as a result of which the resonant frequencies can be measured with a high degree of precision.

The mass sensitivity at the first resonant frequency is different from the mass sensitivity of the second resonant frequency. The temperature sensitivity at the first resonant frequency is different from the temperature sensitivity of the second resonant frequency. The mass binding $\Delta m$ and the change in temperature $\Delta T$ can be determined computationally by measuring the current resonant frequencies or their shifts with respect to the original resonant frequencies at the start of the measurement at a predefined reference temperature and a predefined reference mass. The measurements of the resonant frequencies are taken sequentially with a minimum possible time offset in each case. A virtually simultaneous measurement of the resonant frequencies is even possible with the aid of digital measurement technology. This also enables rapidly occurring changes in temperature or mass to be determined with a high resolution.

The current mass binding of the substance to be detected to the chemically sensitive layer and/or the current change in temperature can be determined with the aid of the following formulae:

$$\Delta m = \frac{\Delta fR1 * kT2 - \Delta fR2 * kT1}{km2 * kT1 - km1 * kT2} \quad \text{(Equation 1)}$$

$$\Delta T = \frac{\Delta fR1 * km2 - \Delta fR2 * km1}{km2 * kT1 - km1 * kT2|} \quad \text{(Equation 2)}$$

where
$\Delta fR1$: change in the first resonant frequency of the device with respect to a preliminary value or reference value,
$\Delta fR2$: change in the second resonant frequency of the device with respect to a preliminary value or reference value,
km1: mass sensitivity of the first resonant frequency of the device km2: mass sensitivity of the second resonant frequency of the device kT1: the temperature sensitivity of the first resonant frequency of the device kT2: the temperature sensitivity of the second resonant frequency of the device In this case the mass sensitivity is defined as follows:

$$km = \Delta f/\Delta m = cm*fR/m \cong (\text{=proportional to})fR^2 \quad \text{(Equation 3)}$$

where km is the mass sensitivity of the device, fR the resonant frequency of the device without adsorbed substance, cm a material-specific constant, and m the mass of the resonator per unit area, where the mass sensitivity km is proportional to the square of the resonant frequency fR of the device.

The temperature sensitivity kT is defined as follows:

$$kT = \Delta f/\Delta T = cT*fR/T \quad \text{(Equation 4)},$$

where kT is the temperature sensitivity of the device, fR the resonant frequency of the device at a predefined reference temperature T_ref, cT a material-specific constant, and T the temperature of the resonator.

The temperature sensitivity is dependent inter alia on material properties of the device.

The two resonant frequencies are read out alternately or simultaneously for the purpose of capturing the two current resonant frequencies.

The resonator can be excited by means of an alternating electrical field and may be embodied as a film bulk acoustic wave resonator (FBAR) having a piezoelectric element as the active element of the resonator. The alternating field may have a plurality of frequencies in the range of the resonant frequencies simultaneously, as a result of which the most important resonant frequencies of the device are excited continuously. This enables the evaluation unit for electrically driving the resonator and for measuring the resonant frequencies to measure the resonant frequencies in rapid alternation or even (almost) simultaneously.

The mass binding and the temperature are calculated from the two measured resonant frequencies, wherein in particular the concentration of a substance from a fluid can be measured from the mass binding. An almost delay-free acquisition of the temperature and/or change in mass of the device is possible.

The evaluation unit is present either on the carrier or externally.

The temperature of the device is changed, the two resonant frequencies fR1, fR2 of the device being measured continuously in the process, from which
the current temperature T or the change in temperature $\Delta T$ and the current mass binding $\Delta m$ are determined,
as a result of which a multiplicity of biological and chemical processes can be determined, for example the determination of the melting temperature of DNA or the investigation of the thermal resistance of substances, in particular proteins, for example heat shock proteins.

The mass binding is determined with computational elimination of the fluctuations in the temperature, even if the ambient temperature varies or the sensor or device itself heats up.

FIG. 1 shows an example device 20 comprising a preferably piezoelectrically embodied resonator 1 which can be electrically excited into vibrations by way of electrodes 2 arranged on its top side and underside. The thickness of the resonator 1 or of its piezoelectric layer is inversely proportional to the resonant frequency fR of the resonator 1 and is equal to half the resonance wavelength $\lambda$, i.e. $\lambda/2$. The resonator 1 is mounted onto a carrier 10 preferably embodied as a silicon wafer, an acoustic mirror 4 serving to decouple the acoustic waves $\lambda$ generated by the resonator 1 with respect to the carrier 10 being arranged between the resonator 1 and the carrier 10.

A chemically sensitive layer 8 for adsorbing a substance 81 to be detected is applied on the resonator 1 and above or next to the upper electrical conductor 2. The mass adsorbed on the layer 81 increases the total mass of the resonator 1, thereby reducing the resonant frequency fR of the device. A high mass sensitivity km is achieved at a resonant frequency fR of the device 20 in the region of 1 GHz. The definition of the mass sensitivity km is formulated in greater detail in the introduction to the description.

When a fluid is applied to the device 20, whether it be in liquid or gaseous form with substances 81 or types of gas 81 to be detected contained therein, it is possible to determine the mass m of the substance 81 adsorbed on the layer 8 by measuring the frequency change deltafR of the resonant frequency fR. The device 20 therefore constitutes a low-cost sensor having high sensitivity to substances 81 requiring to be detected.

The surface section of the layer 8 can, however, also be provided with a material which is not or not only chemically sensitive, but which exhibits specifically selective or non-selective behavior and/or sorption capability for a substance to be detected or a reaction or hybrid product. Alternatively, the material can be capable of assimilating accumulations or deposits of the aforementioned substances.

Connected to the electrical contacts 2 of the resonator 1 on the device 20 from FIG. 1 is a drive and measurement unit 11 which excites the resonator 1 into vibrating at a predefined frequency f and measures the frequency response of the impedance Z at its respective amplitude or absolute value |Z| and its phase Zphas.

The quality of the resonator 1 is improved with the aid of the acoustic mirror 4, since its losses with respect to the substrate 10 are reduced. The acoustic mirror 4 is embodied as a reflector stack having three pairs of mirror layers 41, 42 in which each arranged pair 41, 42 starting from the resonator 1 may include a layer 41, e.g., consisting of metal, having higher acoustic impedance Z1 and a following, preferably dielectrically embodied layer 42 having low acoustic impedance Z2. The height or thickness of the material 41 having high acoustic impedance Z1 and the thickness of the material 42 having low acoustic impedance are equal in each case to a quarter ($\lambda/4$) of the resonance wavelength $\lambda$ of the resonator 1. The acoustic mirror 4 represents a band elimination filter having a notch frequency fRS which is chosen to be equal to the resonant frequency fR of the resonator 1. This causes the waves of the resonator 1 to be reflected most strongly at its resonant frequency fR, as a result of which the device 20 oscillates with high quality, as illustrated with the aid of the frequency response characteristic of the impedance Z in FIG. 4a.

The frequency ranges around and between the resonant frequencies fR1 and fR2 are selected by the drive and measurement unit 11 in rapid succession or simultaneously with the aid of a multifrequency spectrum in the range of the resonant frequencies fR1 and fR2, such that the current resonant frequencies fR1, fR2 are measured repeatedly, preferably at a maximally high repetition frequency of several Hz up to several thousand Hz. Higher repetition frequencies are also possible with digital measurement sensors. The two unknowns "mass binding $\Delta m$" and "change in temperature $\Delta T$" can consequently be extracted with the aid of the aforementioned formulae.

FIG. 4a shows the impedance Z with its absolute value |Z| (ohmic resistance) and its phase Zphas as a function of the frequency f of the device 20 from FIG. 1. In this case the resonant frequency fR of the device 20 lies at just under 800 MHz, the bandwidth B at approximately 20 MHz being small in relation to the resonant frequency fR, which is equivalent to a high oscillation quality of the device 20. The phase response with the phase ZPhas(f) represents the typical waveform when a resonance occurs in the frequency response.

Also shown in FIG. 1 is the waveform of a wave 9 generated by the resonator 1 and running in the mirror 4, which wave 9 starting from the top surface with the layer 8 of the resonator 1 in a wave crest by $\lambda/2$ likewise borders in a wave crest on the acoustic mirror 4. The wave 9 runs further in the direction of the carrier 10 and passes the layers 41, 42, 41, 42, 41, 42, each $\lambda/4$ thick, until the attenuated wave 9 has reached the carrier 10. Some of the wave energy of the wave 9 is reflected in the direction of the resonator 1 at each of the boundary surfaces of the layers 41, 42 and 42, 41.

Figure 2:
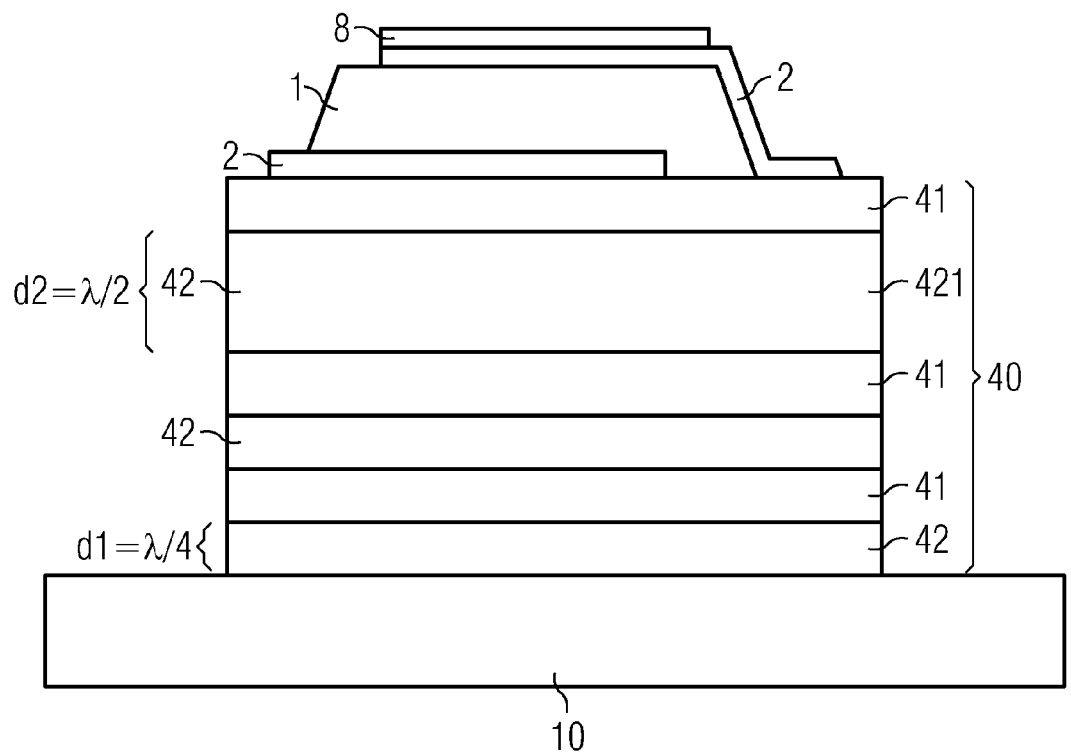
FIG. 2 shows a variant of the example device of FIG. 1 having a detuned acoustic mirror.

FIG. 2 shows a device 20 from FIG. 1 in which, in contradistinction to FIG. 1, the first (starting from the resonator 1) low-impedance layer 42, 421 having lower impedance Z2 has a layer thickness of $\lambda/2$. The remaining layers 41, 42 retain their layer thicknesses from FIG. 1.

As a result the band elimination filter 4 from FIG. 1 is detuned such that a band elimination filter 40 having two notch frequencies fRS1 and fRS2 is produced. Or expressed in different terms: Two series-connected band elimination filters are produced having a first notch frequency fRS1 and a second notch frequency fRS2 in each case. The acoustic mirror 40 in this case blocks not just at a notch frequency fRS as in FIG. 1, but at two more or less tightly adjacent notch frequencies fRS1 and fRS2.

In the frequencies f lying between the two notch frequencies fRS1 and fRS2 and/or outside of the same, the mirror 40 allows the acoustic waves 9 to pass through so strongly to the carrier 10 that the wave energy losses become so high that no resonance of the acoustic resonator 1 can become established there. The resonant frequency fR of the resonator 1 from FIG. 1 is shifted in FIG. 2 due to acoustic coupling of the resonator 1 to the acoustic mirror 40 in the direction of the notch frequencies fRS1 and fRS2. Two "new" resonant frequencies fR1 and fR2 of the device 20 from FIG. 2 are produced, the resonant frequency fR1 of the resonator 1 preferably lying between the resonant frequencies fR1 and fR2.

Figure 4B:
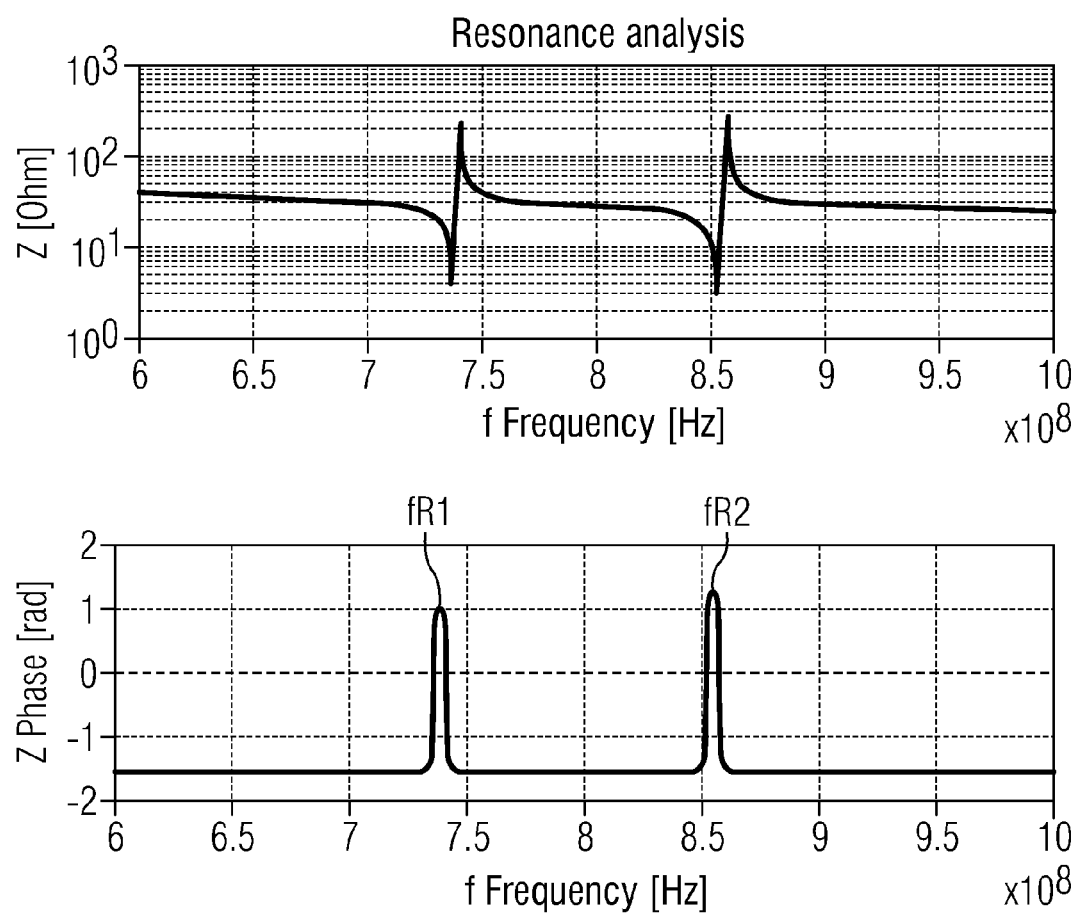
FIG. 4b is a diagram representing the impedance-frequency dependence of the example device of FIG. 2.

FIG. 4b shows the impedance Z with its absolute value |Z| (ohmic resistance) and its phase Zphas as a function of the frequency f of the device 20 from FIG. 2. In this case the resonant frequencies fR1 and fR2 lie at approximately 740 MHz and 860 MHz, with the resonant frequency fR of the device 20 from FIG. 1 lying between these at approximately 800 MHz. The phase response with the phase ZPhas(f) represents the typical waveform when resonances occur in the frequency response.

FIG. 3 shows a device 20 from FIG. 1 in which, in contradistinction to FIG. 1, the second (starting from the resonator 1) low-impedance layer 42, 422 having lower impedance Z2 has a layer thickness of $\lambda/2$. The remaining layers 41, 42 retain their layer thicknesses from FIG. 1.

As a result the band elimination filter 4 from FIG. 1 is detuned such that a band elimination filter 400 having two notch frequencies fRS3 and fRS4 is produced. Or expressed in different terms: Two series-connected band elimination filters are produced having a first notch frequency fRS3 and a second notch frequency fRS4 in each case. The acoustic mirror 400 in this case blocks not just at a notch frequency fRS as in FIG. 1, but at two more or less tightly adjacent notch frequencies fRS3 and fRS4, which lie closer together than the notch frequencies fRS1 and fRS2 from FIG. 2. The layer 422 having the lower impedance (Z2) from FIG. 3 is further away from the resonator 1 in comparison with the layer 421 from FIG. 2, as a result of which the energy of the waves that is available for "detuning" the band elimination filter is already more strongly attenuated due to reflections of a plurality of layers 41, 42 lying thereabove. This causes the band elimination filter 400 from FIG. 3 to be less strongly "detuned" than the band elimination filter 40 from FIG. 2, as a result of which the notch frequencies fRS3 and fRS4 lie closer together.

FIG. 4c shows the impedance Z with its absolute value |Z| (ohmic resistance) and its phase Zphas as a function of the frequency f of the device 20 from FIG. 3. In this case the resonant frequencies fR1 and fR2 lie at approximately 780 MHz and 810 MHz, with the resonant frequency fR of the device 20 from FIG. 1 lying between these at just about 800 MHz. The phase response with the phase ZPhas(f) represents the typical waveform when resonances occur in the frequency response.

FIG. 4d shows a diagram containing measurements of a second embodiment of a device 20 from FIG. 2 which has a somewhat different design and yet similar results as known from FIG. 4b. The resonant frequencies fR5 and fR6 lie at 814 MHz and 838 MHz.

The current mass binding $\Delta m$ of the substance 81 to be detected to the chemically sensitive layer 8 and/or the current change in temperature ($\Delta T$) can be determined from the measured resonant frequencies with the aid of the following formulae by way of example:

$$\Delta m = \frac{\Delta fR1 * kT2 - \Delta fR2 * kT1}{km2 * kT1 - km1 * kT2} \quad \text{(Equation 1)}$$

$$\Delta T = \frac{\Delta fR1 * km2 - \Delta fR2 * km1}{km2 * kT1 - km1 * kT2|} \quad \text{(Equation 2)}$$

where $\Delta fR1$: change in the first resonant frequency fR1 of the device 20 with respect to a preliminary value or reference value, $\Delta fR2$: change in the second resonant frequency fR2 of the device 20 with respect to a preliminary value or reference value, km1: mass sensitivity at the first resonant frequency fR1; fR3 of the device 20 km2: mass sensitivity at the second resonant frequency fR2; fR4 of the device 20 kT1: the temperature sensitivity at the first resonant frequency fR1; fR3 of the device 20 kT2: the temperature sensitivity at the second resonant frequency fR2; fR4 of the device 20.

Multiple $\lambda/2$ layers 41, 42 in succession are particularly easy to produce for reasons relating to manufacturing processes. Preferably only one of the layers 41, 42 is therefore varied in terms of its thickness. Other acoustic mirrors 4, 40, 400 are also conceivable in other embodiment variants, e.g. having layer thicknesses between $\lambda/2$ and $\lambda/4$. In addition the acoustic mirror 4, 40, 400 can have a plurality of layers 41 having higher impedance Z1 with layer thicknesses between $\lambda/4$ and $\lambda/2$.

Tungsten

The material 41 having higher impedance Z1 may be made of metal, preferably of tungsten.

The material 42 having lower impedance Z2 may be embodied from a dielectric material.

Alternatively it is possible to embody devices with acoustic mirrors which have three or more closely adjacent resonant frequencies. This enables more than two unknowns to be extracted, for example mass binding, temperature under the effect of vibrations.

In this case the spacing of the resonant frequencies fR1, fR1 or fR3, fR4 preferably lies in relation to the arithmetic mean of the resonant frequencies fR1, fR1 or fR3, fR4.

What is claimed is:

1. A device for detecting at least one substance, comprising:
   a carrier,
   a resonator applied to the carrier, the resonator having a surface facing away from the carrier,
   a layer for selectively or non-selectively binding with a substance to be detected formed on the surface,
   an acoustic mirror for decoupling acoustic waves of the resonator from the carrier arranged between the carrier and the resonator, wherein the acoustic mirror comprises a band elimination filter system having at least first and second band elimination filters connected in series, each band elimination filter comprising a layer pair including a layer having higher acoustic impedance and a layer having lower acoustic impedance, and
   wherein the lower acoustic impedance layer of the first band elimination filter has a different thickness than the lower acoustic impedance layer of the second band elimination filter, such that the first and second band elimination filters define two adjacent notch frequencies at which the acoustic waves of the resonator are at least partially reflected.

2. The device of claim 1, wherein at almost one hundred percent decoupling from the carrier, the resonant frequency of the resonator lies between the two notch frequencies of the mirror.

3. The device of claim 1, wherein the resonator is acoustically coupled to the carrier via the mirror such that the resonant frequency of the device is detuned from the resonant frequency of the resonator in the direction of the two notch frequencies of the mirror to a first and a second resonant frequency of the device.

4. The device of claim 1, wherein the resonator has a thickness equivalent to half the resonance wavelength of the resonator at almost one hundred percent decoupling from the carrier.

5. The device of claim 1, wherein for the second elimination band filter, each of the lower acoustic impedance layer and the higher lower acoustic impedance layer has a thickness approximately equivalent to a quarter of the wavelength of the resonant frequency of the resonator, and
   wherein for the first elimination band filter, the lower acoustic impedance layer has a thickness between a quarter and half of the inverse of the resonant frequency of the resonator.

6. The device of claim 5, wherein starting from the resonator the layer having the greater thickness represents the second, fourth or sixth layer.

7. The device of claim 1, wherein the resonator is excitable by electrical energy, contains a piezoelectric element as the active element, and is embodied as a film bulk acoustic wave resonator (FBAR), the resonator being provided with electrical terminals to allow the electrical energy to be supplied.

8. The device of claim 1, comprising an evaluation unit for electrically driving the resonator and for measuring the current frequency at a given time.

9. The device of claim 1, wherein the difference between the two resonant frequencies of the device lies between a seventh and a twentieth of the arithmetic mean of the two resonant frequencies.

10. The device of claim 1, wherein the mass sensitivity at the first resonant frequency is different from the mass sensitivity of the second resonant frequency, and/or the temperature sensitivity at the first resonant frequency is different from the temperature sensitivity of the second resonant frequency, such that the mass binding ($\Delta m$) and the change in temperature ($\Delta T$) can be determined by measuring the current resonant frequencies or their shifts ($\Delta fR1$, $\Delta fR2$) with respect to predefined reference resonant frequencies at a predefined reference temperature and a predefined reference mass, wherein the measurements of the resonant frequencies are taken sequentially with a negligible time offset in each case, negligible without a change in temperature and/or change in mass occurring in this time period.

11. The device of claim 10, wherein the current mass binding ($\Delta m$) of the substance to be detected to the layer and/or the current change in temperature ($\Delta T$) can be determined with the aid of the following formulae:

$$\Delta m = \frac{\Delta fR1 * kT2 - \Delta fR2 * kT1}{km2 * kT1 - km1 * kT2} \quad \text{(Equation 1)}$$

$$\Delta T = \frac{\Delta fR1 * km2 - \Delta fR2 * km1}{km2 * kT1 - km1 * kT2|} \quad \text{(Equation 2)}$$

where
$\Delta fR1$: change in the first resonant frequency of the device with respect to a preliminary value or reference value,
$\Delta fR2$: change in the second resonant frequency of the device with respect to a preliminary value or reference value,
km1: mass sensitivity at the first resonant frequency of the device,
km2: mass sensitivity at the second resonant frequency of the device,
kT1: the temperature sensitivity at the first resonant frequency of the device, and
kT2: the temperature sensitivity at the second resonant frequency of the device.

12. The device of claim 10, wherein the mass sensitivity km is defined as follows:

$$km = \Delta f/\Delta m = cm * fR/m \approx fR^2$$

where km is the mass sensitivity of the device, fR the resonant frequency of the device without adsorbed substance, cm a material-specific constant, and m the mass of the resonator per unit area, the mass sensitivity km being proportional to the square of the resonant frequency fR of the device;
the temperature sensitivity kT is defined as follows:

$$kT = \Delta f/\Delta T = cT * fR/T$$

where kT is the temperature sensitivity of the device, fR the resonant frequency of the device at a predefined reference temperature (T_ref), cT a material-specific constant, and T the temperature of the resonator or of the device.

13. The device of claim 1, wherein the band elimination filter system of the acoustic mirror includes three or more band elimination filters connected in series, including the first and second band elimination filters.

14. A device for detecting at least one substance, comprising:
   a carrier,
   a resonator applied to the carrier, the resonator having a surface facing away from the carrier, a layer for selectively or non-selectively binding with a substance to be detected formed on the surface, an acoustic mirror for decoupling acoustic waves of the resonator from the carrier arranged between the carrier and the resonator, wherein the acoustic mirror comprises a band elimination filter system having at least first and second band elimination filters connected in series, each band elimination filter comprising a layer pair including a layer having higher acoustic impedance and a layer having lower acoustic impedance, and wherein the higher acoustic impedance layer of the first band elimination filter has a different thickness than the higher acoustic impedance layer of the second band elimination filter, such that the first and second band elimination filters define two adjacent notch frequencies at which the acoustic waves of the resonator are at least partially reflected.

15. The device of claim 14, wherein at almost one hundred percent decoupling from the carrier, the resonant frequency of the resonator lies between the two notch frequencies of the mirror.

16. The device of claim 14, wherein the band elimination filter system of the acoustic mirror includes three or more band elimination filters connected in series, including the first and second band elimination filters.

* * * * *